United States Patent [19]
Battistini et al.

[11] Patent Number: 5,905,149
[45] Date of Patent: May 18, 1999

[54] SUBSTITUTED QUINOLYMETHYLEN-OXINDOLE ANALOGUES AS TYROSINE KINASE INHIBITORS

[75] Inventors: Carlo Battistini; Antonella Ermoli; Sergio Vioglio; Franco Buzzetti; Dario Ballinari, all of Milan, Italy

[73] Assignee: Pharmacia & Upjohn S.p.A, Milan, Italy

[21] Appl. No.: 08/983,516

[22] PCT Filed: May 15, 1997

[86] PCT No.: PCT/EP97/02673

§ 371 Date: Jan. 29, 1998

§ 102(e) Date: Jan. 29, 1998

[87] PCT Pub. No.: WO97/46551

PCT Pub. Date: Dec. 11, 1997

[30]  Foreign Application Priority Data

Jun. 6, 1996 [GB] United Kingdom ............... 9611797

[51] Int. Cl.$^6$ .................. A61K 31/47; A61K 31/535; C07D 401/02; C07D 413/14
[52] U.S. Cl. ............. 544/128; 514/235.2; 514/314; 546/174; 546/176; 546/177
[58] Field of Search ............ 544/128; 546/174, 546/177; 514/314

[56] References Cited

FOREIGN PATENT DOCUMENTS

| WO 91/13055 | 9/1991 | WIPO. |
|---|---|---|
| WO 95/01349 | 1/1995 | WIPO. |
| WO 95/17181 | 6/1995 | WIPO. |
| WO 96/16964 | 6/1996 | WIPO. |
| WO 96/22976 | 8/1996 | WIPO. |

*Primary Examiner*—Robert W. Ramsner
*Attorney, Agent, or Firm*—Oblon, Spivak, McClelland, Maier & Neustadt, P.C.

[57] ABSTRACT

Quinolylmethylen-oxindole derivatives having general formula (I), wherein R is H or —$(CH_2)_n$—$COR_7$ group in which n is an integer of 1 to 4 and $R_7$ is hydroxy, amino, $C_1$–$C_6$ alkoxy or —$NR_5R_6$ in which one of $R_5$ and $R_6$ is hydrogen or $C_1$–$C_6$ alkyl and the other is $C_1$–$C_6$ alkyl or $R_5$ and $R_6$ taken together with the N atom to which they are linked form a 5 to 7 membered saturated heteromonocycle or $R_7$ is a N-terminally linked peptidyl residue containing from 1 to 3 aminoacids in which the terminal carboxyl group may be present as such, as amide, as alkali metal salt or as a $C_1$–$C_4$ alkyl ester, one or two of $R_1$, $R_2$, $R_3$ and $R_4$, which may be the same or different, are selected from: a) —X—$(CH_2)_m$—$NH_2$, —X—$(CH_2)_m$—$NR_5R_6$ or —X—$(CH_2)_m$—$NHR_8$ group; b) —NH—C(=NH)—$NR_5R_6$, —NH—C(=NH)—$NHR_8$, —N=CH—$NH_2$, —N=CH—$NR_5R_6$ or —N=CH—$NHR_8$ group; c) —X—$(C_2)_n$—$COR_7$ group; d) —$COR_a$ or —$COR_9$ group; e) —Y—CO—Y'—$R_{10}$ group; and f) —$NHR_8$ or —$NHR_{11}$ group and the pharmaceutically acceptable salts thereof, are tyrosine kinase inhibitors.

7 Claims, No Drawings

SUBSTITUTED QUINOLYMETHYLEN-OXINDOLE ANALOGUES AS TYROSINE KINASE INHIBITORS

This application is a 371 of PCT/EP97/02673 filed May 15, 1997.

The present invention relates to new derivatives of substituted quinolylmethylen-oxindoles, to a process for their preparation, to pharmaceutical compositions containing them and to their use as therapeutic agents, in particular as tyrosine kinase inhibitors.

International applications WO91/13055 and WO95/01349 disclose quinolylmethylen-oxindole derivatives endowed with high in vitro tyrosine kinase inhibiting activity. However, such quinolylmethylene-oxindole derivatives, similarly to other known tyrosine kinase inhibitors, are characterized by high lipophylicity, low aqueous solubility and consequently low bioavailability.

However, the task to combine in the same molecule a high tyrosine kinase inhibiting activity and adequate hydrosolubility cannot be achieved by merely introducing hydrophilic groups into the structure of in vitro active tyrosine kinase inhibitors, as this strategy results in most cases in a significant loss of inhibitory activity. Indeed, as known in the art, the therapeutic efficacy of all drugs is strongly influenced by different parameters that can affect their bioavailability. Object of the present invention is therefore to provide novel quinolylmethylen-oxindole compounds endowed with improved bioavailability.

Accordingly, the present invention provides novel substituted quinolylmethylen-oxindole derivatives having the following general formula (I)

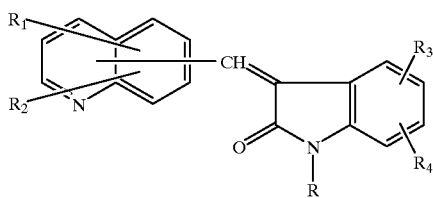

wherein

R is H or —$(CH_2)_n$—$COR_7$ group in which n is an integer of 1 to 4 and $R_7$ is hydroxy, amino, $C_1$–$C_6$ alkoxy or —$NR_5R_6$ in which one of $R_5$ and $R_6$ is hydrogen or $C_1$–$C_6$ alkyl and the other is $C_1$–$C_6$ alkyl or $R_7$ and $R_6$ taken together with the N atom to which they are linked form a 5 to 7 membered saturated heteromonocycle or $R_7$ is a N-terminally linked peptidyl residue containing from 1 to 3 aminoacids in which the terminal carboxyl group may be present as such, as amide, as alkali metal salt or as a $C_1$–$C_4$ alkyl ester; one or two of $R_1$, $R_2$, $R_3$ and $R_4$ are a substituent selected independently from:

a) —X—$(CH_2)_m$—$NH_2$, —X—$(CH_2)_m$—$NR_5R_6$ or —X—$(CH_2)_m$—$NHR_8$ group, in which X is —O—, —S— or —NH—, m is an integer of 2 to 4, $R_5$ and $R_6$ are as defined above, and $R_8$ is $C_2$–$C_6$ alkanoyl or a C-terminally linked peptidyl residue containing from 1 to 3 aminoacids wherein the terminal amino group is either free or protected or in an alkylated form to provide a —$NR_5R_6$ group in which $R_5$ and $R_6$ are as defined above;

b) —NH—C(=NH)—$NR_5R_6$, —NH—C(=NH)—$NHR_8$, —N=CH—$NH_2$, —N=CH—$NR_5R_6$ or —N=CH—$NHR_8$ group in which $R_5$, $R_6$ and $R_8$ are as defined above;

c) —X—$(CH_2)_n$—$COR_7$ group wherein X and $R_7$ are as defined above and n is an integer of 1 to 4;

d) —$COR_a$ or —$COR_9$ group in which $R_a$ is a N-terminally linked peptidyl residue containing from 1 to 3 aminoacids in which the terminal carboxyl group may be present as such, as amide, as alkali metal salt or as a $C_1$–$C_4$ alkyl ester and $R_9$ is a —$(CH_2)_p$—$NH_2$, —$(CH_2)_p$—$NR_5R_6$ or —$(CH_2)_p$—$NHR_8$ group in which p is 1 or 2 and $R_5$, $R_6$ and $R_8$ are as defined above;

e) —Y—CO—Y'—$R_{10}$ group wherein each of Y and Y' (which may be same or different) is —NH— or —O— and $R_{10}$ is phenyl or $C_1$–$C_6$ alkyl unsubstituted or substituted by phenyl; and f) —$NHR_8$ or —$NHR_{11}$ group in which $R_8$ is as defined above and $R_{11}$ is an amino protective group; and the others of $R_1$, $R_2$, $R_3$ and $R_4$ are independently chosen from hydrogen, halogen, amino, hydroxy, $C_1$–$C_6$ alkyl, $C_1$–$C_6$ alkoxy, phenyl-($C_1$–$C_6$)alkoxy, carboxy, $C_1$–$C_6$ alkoxycarbonyl, $C_2$–$C_6$ alkanoyloxy, cyano and —$NR_5R_6$ in which $R_5$ and $R_6$ are as defined above, and the pharmaceutically acceptable salts of salt forming compounds of formula (I).

The invention includes within its scope all the possible isomers, stereoisomers and in particular Z- and E-isomers and their mixtures, and the metabolites and the metabolic precursors or bio-precursors (otherwise known as prodrugs) of the compounds of formula (I).

The oxindolidene substituent and $R_1$ and $R_2$ substituents may be independently on either of the benzene and pyridine moieties of the quinoline ring. The oxindolidene substituent is preferably linked to positions 4 or 5 of the quinoline ring.

A —$(CH_2)_m$— or —$(CH_2)_n$— group may be a branched or straight alkylene chain, typically —$CH(CH_3)$—, —$CH_2CH_2$— and $(CH_3)_2CH$—CH<, in particular —CH($CH_3$)— or typically —$CH_2$—, —$CH(CH_3)$—, —$CH_2$—$CH_2$— and $(CH_3)_2CH$—CH=, in particular —$CH_2$— and —$CH(CH_3)$—, respectively.

The alkyl groups, and the alkyl moiety in the alkanoyl groups, may be branched or straight alkyl chains.

A $C_1$–$C_6$ alkyl group is preferably a $C_1$–$C_4$ alkyl group, e.g. methyl, ethyl, propyl, isopropyl, butyl, sec-butyl or tert-butyl, in particular methyl or ethyl.

A $C_1$–$C_6$ alkoxy group is e.g. methoxy, ethoxy, propoxy, isopropoxy, butoxy or tert-butoxy, preferably methoxy, ethoxy or propoxy.

A phenyl-($C_1$–$C_6$)alkoxy group is e.g. benzyloxy, phenethyloxy or phenylpropyloxy, preferably benzyloxy.

When $R_5$ and $R_6$ taken together with the nitrogen atom to which they are linked form a 5 to 7 membered saturated heteromonocycle, said ring can optionally contain a further heteroatom chosen from nitrogen, oxygen and sulphur. Typically said ring is a pyrrolidine, piperidine or morpholine ring.

Examples of aminoacids, which form the peptidyl residue according to the meaning of $R_a$, $R_7$ and $R_8$ as given above, are alanine, glycine, histidine, threonine, glutamic acid, aspartic acid and tyrosine; preferably glycine, alanine, threonine and glutamic acid.

Accordingly, the $R_8$ peptidyl residue may be selected, for instance, from the groups including —CO—CH($CH_3$)—$NH_2$, —CO—CH($CH_3$)—NHCO—CH($CH_3$)—$NH_2$, —CO—CH($NH_2$)—CHOH—$CH_3$, —CO—CH($NH_2$)—$CH_2$—$CH_2$—COOH, —CO—$CH_2$—$NH_2$, —CO—$CH_2$—NH—CO—$CH_2$—$NH_2$, —CO—CH(CHOH—$CH_3$)—NH—CO—CH($NH_2$)—CHOH—$CH_3$, and —CO—CH ($CH_2$—$CH_2$—COOH)—NH—CO—CH($NH_2$)—$CH_2$—$CH_2$—COOH, in which the terminal amino group may be either free or in a protected or alkylated form as stated above.

Similarly the $R_a$ or $R_7$ peptidyl residues are for instance a group selected independently from —NH—CH($CH_3$)—COOH, —NH—$CH_2$—COOH, —NH—CH(COOH)—CHOH—$CH_3$, —NH—CH($CH_3$)—CONH—CH($CH_3$)—COOH, —NH—CH(COOH)—$CH_2$—$CH_2$—COOH, —NH—CH(COOH)—$CH_2$—COOH and —NH—CH(COOH)—$CH_2$—Ph.

When $R_8$ is a C-terminally linked peptidyl residue group as defined above in which the terminal amino group is in a protected form, said amino group may be protected in a conventional way as known from the chemistry of peptides. Typically by an amino protecting group chosen from benzyloxycarbonyl, p-methoxybenzyloxycarbonyl, tert-butoxycarbonyl (BOC), biphenylisopropoxycarbonyl (BBOC), 9-fluorenylmethoxycarbonyl (Fmoc), triphenylmethyl (Trityl), O-nitrobenzenesulfenyl (Nps), trimethylsilylethoxycarbonyl, di-p-nitrophenylethoxycarbonyl and trichloroethoxycarbonyl (Troc). Preferably said amino protecting group being chosen from t-butoxycarbonyl (BOC) and 9-fluorenylmethoxycarbonyl (Fmoc).

$R_{11}$ as an amino protective group may be one of the protecting groups mentioned hereabove.

A metal salt of the terminal carboxyl group of an amino acid is is typically a sodium or potassium salt.

When $R_{10}$ is $C_1$–$C_6$ alkyl substituted by phenyl, it is preferably a phenyl-($C_1$–$C_4$) alkyl group, in particular benzyl or phenethyl.

A halogen atom is for instance fluorine, chlorine, bromine or iodine, preferably a fluorine, chlorine or bromine atom. A $C_2$–$C_6$ alkanoyl group or an alkanoyl moiety in alkanoyloxy groups is preferably a $C_2$–$C_4$ alkanoyl group, in particular acetyl, propionyl or butyryl.

Pharmaceutically acceptable salts of the compounds of the invention include acid addition salts with inorganic acids, e.g. nitric, hydrochloric, hydrobromic, sulphuric, perchloric and phosphoric acid or organic acids, e.g. acetic, trifluoracetic, propionic, glycolic, lactic, oxalic, malonic, malic, maleic, tartaric, citric, benzoic, cinnamic, mandelic and salicylic acid, and salts with inorganic bases, e.g. alkali metal, especially sodium or potassium bases or alkaline earth metal, especially calcium or magnesium bases, or with organic bases, e.g. alkylamines, preferably triethylamine.

As stated above, the present invention also includes within its scope pharmaceutically acceptable bio-precursors, otherwise known as prodrugs of the compounds of formula (I), i.e. compounds which have different formula to formula (I) above but which, nevertheless, upon administration to a human being are converted directly or indirectly in vivo into a compound of formula (I).

Preferred compounds of the invention are the compounds of formula (I), wherein

R is H or —($CH_2$)$_n$—$COR_7$ group in which n is 1 and $R_7$ is hydroxy, amino, $C_1$–$C_4$ alkoxy or $R_7$ is a N-terminally linked peptidyl residue containing 1 to 2 aminoacids in which the terminal carboxyl group is present as alkali metal salt or as a $C_1$–$C_4$ alkyl ester;

one of $R_1$, $R_2$, $R_3$ and $R_4$ is independently a substituent selected from a') —X—($CH_2$)$_m$—$NH_2$, —X—($CH_2$)$_m$—$NR_5R_6$ or —X—($CH_2$)$_m$—$NHR_8$ in which X is —NH—, m is 2, one of $R_5$ and $R_6$ is $C_1$—$C_4$ alkyl and the other is hydrogen or $C_1$–$C_4$ alkyl or $R_5$ and $R_6$ taken together with the nitrogen atom to which they are linked form a morpholine ring, and $R_8$ is a C-terminally linked peptidyl residue containing 1 or 2 aminoacids in which the terminal amino group is present as such;

b') —NH—C(=NH)—$NR_5R_6$, —N=CH—$NR_5R_6$ in which one of $R_5$ and $R_6$ is $C_1$–$C_4$ alkyl and the other is hydrogen or $C_1$–$C_4$ alkyl;

c') —X—($CH_2$)$_n$—$COR_7$ in which X is —O—, n is 1 or 2, $R_7$ is hydroxy, $C_1$–$C_6$ alkoxy, amino or a N-terminally linked peptidyl residue containing 1 or 2 aminoacids;

d') —$COR_a$ group in which $R_a$ is as defined above; and f') —$NHR_8$ or —$NHR_{11}$ in which $R_8$ is $C_2$–$C_4$ alkanoyl or a C-terminally linked peptidyl residue containing 1 or 2 aminoacids and $R_{11}$ is an amino protecting group; and the others of $R_1$, $R_2$, $R_3$ and $R_4$ are independently chosen from hydrogen, halogen, amino, hydroxy, $C_1$–$C_4$ alkyl, $C_1$–$C_4$ alkoxy, phenyl-($C_1$–$C_4$) alkoxy, $C_1$–$C_4$ alkoxy-carbonyl, $C_2$–$C_4$ alkanoyloxy, cyano and $C_1$–$C_4$ alkylamino or di-$C_1$–$C_4$ alkylamino;

and the pharmaceutically acceptable salts of salt forming compounds of formula (I).

Examples of preferred specific compounds of formula (I) are the following compounds:

5-[2-(dimethylamino)ethylamino]-3-(4-quinolylmethylen)-2-oxindole;

5-[2-(morpholino)ethylamino]-3-(4-quinolylmethylen)-2-oxindole;

5-[2-(glycylamino)ethylamino]-3-(4-quinolylmethylen)-2-oxindole;

5-(3,3-dimethylguanidino)-3-(4-quinolylmethylen)-2- oxindole;

5-(dimethylaminomethylenamino)-3-(4-quinolylmethylen)-2-oxindole;

2-[5-(2-oxindol-3-ylidenemethyl)quinol-8-yloxy]propionic acid ethyl ester;

2-[5-(2-oxindol-3-ylidenemethyl)quinol-8-yloxy]propionic acid;

2-[5-(2-oxindol-3-ylidenemethyl)quinol-8-yloxy] propionamide;

N-{2-[5-(2-oxindol-3-ylidenemethyl)quinol-8-yloxy] propionyl} alanine methyl ester;

N-{2-[5-(2-oxindol-3-ylidenemethyl)quinol-8-yloxy] propionyl} alanine;

2-[5-(2-oxindol-3-ylidenemethyl)quinol-8-yloxy] acetic acid ethyl ester;

2-[5-(2-oxindol-3-ylidenemethyl)quinol-8-yloxy] acetic acid;

N-{2-[5-(2-oxindol-3-ylidenemethyl)quinol-8-yloxy] acetyl} alanine methyl ester;

N-{2-[5-(2-oxindol-3-ylidenemethyl)quinol-8-yloxy] acetyl} alanine;

N-[3-(8-hydroxyquinol-5-ylmethylen)-2-oxindol-5-ylcarbonyl] glycinamide;

5-(2-piperidylacetyl)-3-(8-hydroxyquinol-5-ylmethylen)-2-oxindole;

N-[3-(8-hydroxyquinol-5-ylmethylen)-2-oxindol-5-ylcarbonyl] alaninamide;

5-(t-butoxycarbonylamino)-3-(8-hydroxyquinol-5-ylmethylen)-2-oxindole;

5-(glycylamino)-3-(8-hydroxyquinol-5-ylmethylen)-2-oxindole;

5-(alanylamino)-3-(8-hydroxyquinol-5-ylmethylen)-2-oxindole;

5-(threonylamino)-3-(8-hydroxyquinol-5-ylmethylen)-2-oxindole;

5-(glutamylamino)-3-(8-hydroxyquinol-5-ylmethylen)-2-oxindole;

2-[3-(8-benzyloxyquinol-5-ylmethylen)-2-oxindol-1-yl] acetic acid ethyl ester;

2-[3-(8-benzyloxyquinol-5-ylmethylen)-2-oxindol-1-yl] aetic acid;

N-{2-[3-(8-benzyloxyquinol-5-ylmethylen)-2-oxindol-1-yl] acetyl} alanine methyl ester; and N-{2-[3-(8-hydroxyquinol-5-ylmethylen)-2-oxindol-1-yl] acetyl} alanine methyl ester; and the pharmaceutically acceptable salts of salt forming members of the group.

The compounds of formula (I), and the salts thereof, can be obtained by a process comprising:

A) reacting an aldehyde of formula (II)

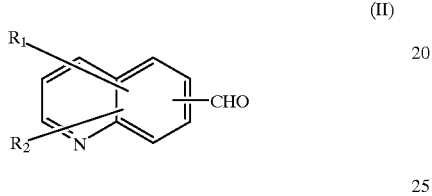

(II)

wherein $R_1$ and $R_2$ are as defined above, with a compound of formula (III)

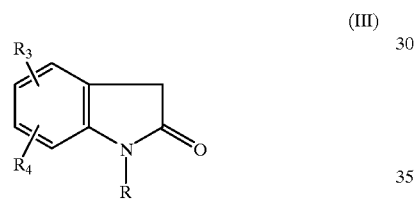

(III)

wherein R, $R_3$ and $R_4$ are as defined above; or

B) reacting a compound of formula (IV)

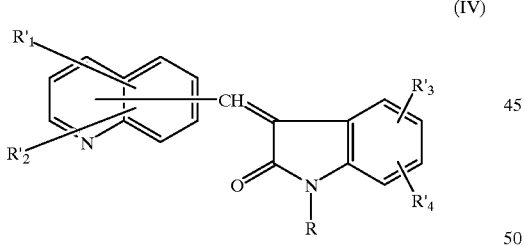

(IV)

wherein one or two of $R'_1$, $R'_2$, $R'_3$ and $R'_4$ are OH, —$NH_2$ or —SH and the others are as R, $R_1$, $R_2$, $R_3$ and $R_4$ as defined above, with an alkylating agent of formula (V) selected from Z—$(CH_2)_m$—$NH_2$;

Z—$(CH_2)_m$—$NR_5R_6$;

Z—$(CH_2)_m$—$NHR_8$ and

Z—$(CH_2)_n$—$COR_7$;

in which Z is a halogen atom and m, n, $R_5$, $R_6$, $R_7$ and $R_8$ are as defined above, thus obtaining a compound of formula (I) wherein one or two of $R_1$, $R_2$, $R_3$ and $R_4$ are as defined above under a) or c); or C) reacting a compound of formula (VI)

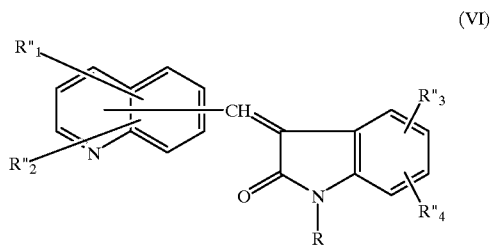

(VI)

wherein one or two of R", $R''_2$, $R''_3$ and $R''_4$ are —OH or —$NH_2$ and the others are as $R_1$, $R_2$, $R_3$ and $R_4$ as defined above, with an acylating agent of formula (VII) selected from

HOOC—Y'—$R_{10}$     (VII)

or a reactive carboxyl derivative thereof, wherein Y' and $R_{10}$ are as defined above, thus obtaining a compound of formula (I) wherein one or two of $R_1$, $R_2$, $R_3$ and $R_4$ are as defined above under e);

D) reacting a compound of formula (VIII)

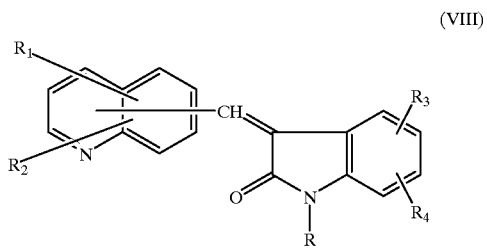

(VIII)

wherein R is H and $R_1$, $R_2$, $R_3$ and $R_4$ are as defined above, with an alkylating agent of formula (IX)

Z—$(CH_2)_n$—$COR_7$     (IX)

wherein Z, n and $R_7$ are as defined above, thus obtaining a compound of formula (I) wherein R is a —$(CH_2)_n$—$COR_7$ group;

E) reacting a compound of formula (X)

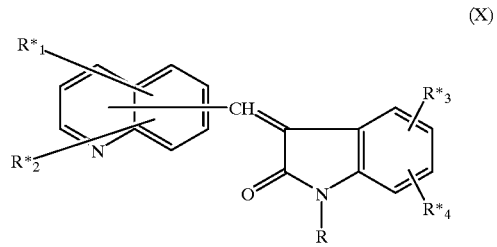

(X)

wherein one or two of $R^*_1$, $R^*_2$, $R^*_3$ and $R^*_4$ are amino or carboxy and the others are as $R_1$, $R_2$, $R_3$ and $R_4$ as defined above, with a peptide compound of formula $R_8H$ and $R_aH$, wherein $R_8$ and $R_a$ are peptidyl residues as defined above, thus giving compounds of formula (I), wherein one or two of $R_1$, $R_2$, $R_3$ and $R_4$ are as defined above under f) and d) respectively; and, if desired, converting a compound of formula (I) into another compound of formula (I), and/or, if desired, converting a compound of formula (I) into a pharmaceutically acceptable salt thereof, and/or, if desired, converting a salt of a compound of formula (I) into a free compound of formula (I), and/or, if desired, separating a mixture of isomers of a compound of formula (I) into the single isomers.

The reaction of a compound of formula (II) with a compound of formula (III) is an analogy process which can be carried out according to known methods as herebelow described; preferably in the presence of a basic catalyst, e.g. pyridine, piperidine, dimethylamine, or a suitable alkali metal hydroxide or alkoxide. For example the reaction of a compound of formula (II) with a compound of formula (III) may be carried out under the conditions of the Knoevenagel reaction as described e.g. by G. Jones in Organic Reactions 15, 204 (1967). Suitable catalysts are organic bases such as pyridine, piperidine or diethylamine. The condensation may be performed in an inert organic solvent, e.g. pyridine, ethanol, methanol, benzene, or dioxane at temperatures ranging from about 0 to about 100° C. Preferably the reaction is carried out in warm ethanol solution in the presence of a piperidine catalyst.

In a compound of formula (V) the halogen atom Z is for instance iodine, bromine or chlorine, preferably bromine. The alkylation of a compound of formula (IV) can be carried out according to known methods, for instance by salification with sodium hydride and then reaction with the bromide of formula (V) in a high boiling aromatic solvent such as xylene. A reactive derivative of a carboxylic acid of formula (VII) is for instance an acyl halide or an anhydride (typically a mixed anhydride) or an in situ generated activated form of the carboxylic acid with a coupling reagent such as benzotriazol-1-yloxy-tripyrrolidinophosphonium hexafluorophosphate (PyBOP). The acylation reaction of a compound of formula (VI) with a compound of formula (VII) is preferably carried out in the presence of a basic agent such as pyridine, at a temperature ranging from about 0 to about 50° C. The alkylation of a compound of formula (VIII) with a compound of formula (IX) can be carried out according to known methods, for instance as described above in method B). But in general milder reaction conditions are applied. Thus the amidic NH can be alkylated with an a-haloacid derivative, preferably α-bromoacid derivative, in a dipolar aprotic solvent such as DMF or acetone and in the presence of an inorganic base such as potassium carbonate at temperatures ranging from room to reflux temperatures.

The reaction of a compound of formula (X) with a compound of formulae $R_8H$ or $R_aH$ according to process E) can be carried out by the same reaction conditions as described above under process C).

A compound of formula (I) can be converted into another compound of formula (I) according to known methods. For instance, a compound of formula (I) in which one or two of $R_1$, $R_2$, $R_3$ and $R_4$ are carboxy and the others are as defined above, can be converted into a corresponding compound of formula (I) wherein one or two of $R_1$, $R_2$, $R_3$ and $R_4$ are a —$COR_a$ group in which $R_a$ is as defined above under d), by acylation reaction of an activated carboxyl derivative with a suitable aminoacid or peptide in an organic solvent, e.g. dichloromethane, in the presence of a basic agent such as pyridine or N-methylmorpholine.

A compound of formula (I) wherein one or two of $R_1$, $R_2$, $R_3$ and $R_4$ are amino and the others are as defined above, can be turn converted into another compound of formula (I) in which one or two of $R_1$, $R_2$, $R_3$ and $R_4$ are —NH—C(=NH)—$NH_2$ as described under b) for instance by reaction with di-tert-butoxycarbonyl-thiourea according to known methods. The guanidino substituted compound thus obtained can be in its turn converted into another compound of formula (I) in which one or two of $R_1$, $R_2$, $R_3$ and $R_4$ are a group —NH—C(=NH)—$NR_5R_6$, or —NH—C(=NH)—$NHR_8$ in which one or two of $R_5$ and $R_6$ are $C_1$–$C_6$ alkyl and $R_8$ is as defined above under a), according to well known alkylation or acylation methods, respectively.

Similarly a compound of formula (I) wherein one or two of $R_1$, $R_2$, $R_3$ and $R_4$ are amino and the others are as defined above, can be converted according to known methods into another compound of formula (I) wherein one or two of $R_1$, $R_2$, $R_3$ and $R_4$ are a —N=$CHNR_5R_6$ group described under b). For instance an amino substituted compound can be reacted with a suitable di-($C_1$–$C_6$ alkyl)N—CHO aldehyde in a suitable polar solvent, e.g. a lower alkanol, typically methanol or ethanol, in the presence of a basic agent, such as piperidine, to obtain a —N=$CHNR_5R_6$ compound in which $R_5$ and $R_6$ are $C_1$–$C_6$ alkyl.

A compound of formula (I) wherein R or one or two of $R_1$, $R_2$, $R_3$ and $R_4$ are —X—$(CH_2)_n$—$COR_7$ in which $R_7$ is alkoxy and X and n are as defined above, can be converted into the corresponding compound of formula (I) in which $R_7$ is amino or —$NR_5R_6$ as defined above by aminolysis with $NH_3$ or $NHR_5R_6$ respectively according to well known methods in organic chemistry.

A compound of formula (I) wherein R or one or two of $R_1$, $R_2$, $R_3$ and $R_4$ are —X—$(CH_2)_n$—$COR_7$ in which $R_7$ is OH and X and n are as defined above, can be converted into a compound of formula (I) wherein $R_7$ is a N-terminally linked peptide residue as defined above by using the same methods as in process c).

The optional salification of a compound of formula (I) as well as the conversion of a salt into the free compound and the separation of a mixture of isomers into the single isomers may be carried out by conventional methods. For example, the separation of a mixture of geometric isomers, e.g. cis- and trans-isomers, may be carried out by fractional crystallization from a suitable solvent or by chromatography, either column chromatography or high pressure liquid chromatography. The intermediates of formulae (II) and (III) can be obtained by known methods from known compounds, e.g. as described in WO91/13055 and WO95/01349. The people skilled in the art will appreciate that the intermediates of formula (II) and (III) can be submitted to same substituent chemical modifications as described in connection with the compound of formula (I). However, these substituent modifications can be properly performed at convenience at different levels within the process depending on the nature of the substituents and on the compatibility of the transforming reaction with the involved chemical groups.

The intermediate compounds of formulae (IV)–(X) are known compounds or can be obtained from known compounds. For instance, most of the compounds of formulae (IV), (VI), (VIII) and (X) are known from WO91/13055 and WO95/01349 or can be obtained similarly.

Compounds of formula (III) if not available, can also be obtained from the corresponding indole derivative by an analogy process through known methods. A preferred one is an oxidation-reduction process as described by Marfat et al. in Tetrahedron Letters 28, 4027 (1987) comprising the use of pyridinium bromide perbromide using a tertiary alcohol as solvent, preferably tert-butanol, followed by a reductive step with zinc in acetic acid or hydrogenation in the presence of palladium on charcoal.

When in the new compounds of the present invention and in the intermediate products used for their preparation there are groups present which need to be protected before the above described reactions are performed, they may be protected before the reaction takes place and then deprotected at the end of the reaction, according to well known methods in organic chemistry.

PHARMACOLOGY

The compounds of the invention possess specific tyrosine kinase inhibiting activity. It is believed that tyrosine kinase inhibitors may be of great importance in the control of uncontrolled cellular reproduction, i.e. in cellular reproduction disorders. Hence, the compounds according to the present invention can be useful in the treatment of pathological proliferation disorders in mammals, including humans. Typical examples of such disorders are tumors, including leukemia, and psoriasis. The compounds of the invention can also be useful in inhibiting the development of the atheromatous plaque and in the control of angiogenesis and as anti-metastatic agents.

Recent studies on the molecular basis of the neoplastic transformation have identified a family of genes, designed oncogenes, whose aberrant expression causes tumorigenesis. For example, the RNA tumor viruses possess such an oncogene sequence whose expression determines neoplastic conversion of infected cells. Several of their oncogene-encoded proteins, such as $pp60^{v-src}$, $p70^{gag-yes}$, $p130^{gag-fps}$ and $p70^{gag-fgr}$ display protein tyrosine kinase activity, that is they catalyze the transfer of the γ-phosphate from adenosine triphosphate (ATP) to tyrosine residues in protein substrate. In normal cells, several growth factor receptors, for example the receptors for PDGF, EGF, α-TGF and insulin, display tyrosine kinase activity. Binding of the growth factor (GF) activates the receptor tyrosine kinase to undergo autophosphorylation and to phosphorylate closely adjacent molecules on tyrosine. Therefore, it is thought that the phosphorylation of these tyrosine kinase receptors plays an important role in signal transduction and the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinase can be useful in investigating the mechanism of cancerogenesis, cell proliferation and differentiation and it can be effective in the prevention and chemotherapy of cancer and in other pathological proliferative conditions.

Hence the compounds according to the present invention can be useful in the treatment of pathological proliferation disorders in mammals, including humans.

A human or animal, e.g. a mammal, can thus be treated by a method comprising the administration thereto of therapeutically effective amount of one of the compounds of the invention. In this way the condition of the human or animal may be improved. Amelioration of the disease state or disorder from which the human or animal is suffering can be achieved. Typical examples of such disorders are benign and malignant tumours, including leukaemia such as myeloblastic leukaemia, lymphoma, sarcoma, neuroblastoma, Wilm's tumour, malignant neoplasm of the bladder, breast, lung or thyroid, neoplasias of epithelial origin, such as mammacarcinoma. Moreover, they can be useful in the treatment of epidermal hyperprolifertion, such as psoriasis. The compounds of the invention can also be useful in inhibiting the development of the atheromatous plaque and restenosis, in the control of angiogenesis, as anti-metastatic agents and in treating diabetic complications. They have also utility in the control of immune system diseases, e.g. as immunosuppressants, since protein tyrosine kinases, particularly Zap70, p56lck and p59 fyn, are strongly involved in the control of the proliferation of the immune system. Moreover, the compounds of the invention have utility in the treatment of Alzheimer's disease due to the pivotal role played by tyrosine phosphorylation (e.g., Tau proteins) in the development of this disease.

The tyrosine specific protein kinase activity of the compounds of the invention is shown, e.g., by the fact that they are active in the in vitro and in vivo test described herebelow.

In Vitro Assay p45 v-abl kinase purification

The enzyme used in our tests is the p45 v-abl tyrosine kinase which represents the catalytic domain of the Abelson tyrosine kinase (isolated from the Abelson murine leukemia virus). The p45 v-abl kinase is produced and isolated as described by Wang et al. in J.Biol.Chem. 260, 64 (1985) and by Ferguson et al. in J. Biol. Chem. 260, 3652 (1985) and in Biochem. J. 257, 321 (1989).

p45 v-abl kinase assay $(Val^5)$-angiotensin II phosphorylation is performed, by incubation with 40 ng of purified abl-kinase and $(\gamma$-$^{32}$P) ATP, in 50 μl of buffer containing Tris-HCl 25 mM, pH 8.0, $MgCl_2$ 10 mM and dithiothreitol 0.1 mM (kinase buffer). The reaction mixture is incubated for the indicated time at 30° C. and the reaction stopped by adding 50 μl of 5% trichloracetic acid. After a brief incubation on ice the tubes are centrifuged. The supernatants are spotted on phosphocellulose paper squares (Whatman P-81) and washed extensively in acetic acid. The radioactivity bound to dried phosphocellulose squares is measured in a liquid scintillation counter. $IC_{50}$ values are calculated from triplicated determination of each experimental point. Each inhibitor is tested at concentrations ranging from 0 to 400 μg in the presence of fixed concentrations of peptide (2 mM) and ATP (50 μM).

In Vivo Assay

K562 cell growth inhibition assay

K562 cells, a human myelogenous leukemia cell line, were seeded into a 24 wells tissue culture plate (Falcon 3047) (10000/well) in the presence of increasing concentrations of the compounds. After 72 h, cells were harvested and were counted using a cell counter (Coulter Counter-ZM). The percent of inhibition was evaluated in respect to the untreated control cells.

The inhibitory activity data for a representative compound of the present invention, obtained both in the in vitro p45 v-abl kinase assay and in the in vivo human myeloid leukemia K562 cell growth inhibition assay as described above, are set out in the following table 1.

TABLE 1

| Inhibition of p45 v-abl kinase and K562 cell growth | | |
|---|---|---|
| | $IC_{50}$ (μM) | |
| | v-abl | K562 |
| 2-[5-(2-oxindol-3-ylidenemethyl)quinol-8-yloxy]propionic acid ethyl ester | 15.0 | 39.5 |

As can be appreciated from the activity data shown in table 1, the compound according to the invention is endowed with valuable biological properties.

In every case the water solubility is greater than 10 mg/ml allowing to prepare aqueous solutions with concentration higher than 10 mmol, in striking difference with the previous analogs characterized by low water solubility.

In view of their high activity and low toxicity, the compounds of the invention can be used safely in medicine. The compounds of the invention can be administers in a variety of dosage forms, e.g. orally, in the forms of tablets, capsules, sugar- and film-coated, tablets, liquid solutions or suspensions; rectally, in the form of suppositories; parenterally, e.g. intramuscularly, or by intravenous injection or infusion; or topically. The dosage depends on the age, weight, condition of the patient and administration route. For example, the dosage adopted for oral administration to adult humans for the compound 2-[5-(2-oxindol-3-ylidenemethyl)quinol-8-yloxy] propionic acid ethyl ester may range from about 5 to about 150–200 mg per dose, from 1 to 5 times daily. Of course, these dosage regimes may be adjusted to provide the optimal therapeutic response.

The pharmaceutical compositions containing the compounds of the invention are usually prepared following conventional methods and are administered in a pharmaceutically suitable form. For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, by means of mixing, granulating, tabletting, sugar-coating or film-coating processes. The liquid dispersion, for oral administration may be, e.g., syrups, emulsions and suspensions.

The syrup may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusions may contain as carrier, for example, sterile water or, preferably, they may be in the form of sterile aqueous, isotonic saline solutions.

The suppositories may contain, together with the active compound, a pharmaceutically acceptable carrier, e.g. cocoabutter, polyethylene glycol, a polyoxyethylene sorbitan fatty acid ester surfactant or lecithin.

Compositions for topical application, e.g. creams, lotions or pastes, can be prepared by admixing the active ingredient with a conventional oleaginous or emulsifying excipient.

A further object of the present invention is a combined method of treatment of cancer or of amelioration of the conditions of mammals, including humans, suffering from cancer, said method comprising administering 1) a compound of the invention, that is a compound of formula (I), or a pharmaceutically acceptable salt thereof, and
2) an additional antitumor agent, in amounts and close enough together in time sufficient to produce a therapeutically useful effect.

The present invention also provides products containing a compound of the invention, that is a compound of formula (I) or a pharmaceutically acceptable salt thereof, and an additional antitumor agent as a combined preparation for simultaneous, separate or sequential use in anticancer therapy.

The term "antitumour agent" is meant to comprise both a single antitumour drug and "cocktails", i.e. a mixture of such drugs, according to the clinical practice.

Examples of antitumour agents that can be formulated with a compound of the invention or, alternatively, can be administered in a combined method of treatment, include doxorubicin, daunomycin, epirubicin, idarubicin, etoposide, fluorouracil, melphalan, cyclophosphamide, bleomycin, vinblastin and mitomycin or a mixture of two or more thereof. The compounds of the invention can therefore be used in a treatment to ameliorate a cancer. They may be administered to a patient suffering from a cancer treatable with an antitumour agent, for example an anthracycline glycoside such as doxorubicin, daunomycin, epirubicin or idarubicin as mentioned above, together with the antitumour agent.

A compound of the invention and an antitumour agent such as an anthracycline glycoside can be administered to improve the condition of a patient having leukemia such as myeloblastic leukemia, lymphoma, sarcoma, neuroblastoma, Wilm's tumour or malignant neoplasm of the bladder, breast, lung or thyroid.

Accordingly, the present invention provides a method of treating a patient in need of a tyrosine kinase inhibitor, the method comprising administering to said patient a therapeutically effective amount of a compound of formula (I) as defined above, or a pharmaceutically acceptable salt thereof.

The following examples illustrate but do not limit the invention.

EXAMPLE 1
2-[5-(2-oxindol-3-ylidenemethyl)quinol-8-yloxy]propionic acid ethyl ester A solution of 8-hydroxyquinoline-5-carbaldehyde (346 mg, 2 mmol), 2-oxindole (266 mg, 2 mmol) and piperidine (43 mg, 0.5 mmol) in absolute ethanol (10 ml) was heated for 3 h at 60–70° C. under nitrogen. Then the reaction mixture was chilled and evaporated under vacuum to dryness. The residue was submitted to column chromatography over silica gel using dichloromethane/ethanol 4% as eluant to give pure 3-(8-hydroxy-5-quinolylmethylen)-2-oxindole in 60% yield (365 mg). To a solution of 3-(8-hydroxy-5-quinolylmethylen)-2-oxindole (300 mg, 0.99 mmol) in THF (5 ml) was added at room temperature a solution of 1M tetrabutylammonium fluoride (5 ml) and 2-bromopropionic acid ethylester (0.9 ml, 6.9 mmol). The reaction mixture was stirred at room temperature for another 1 h and then diluted with dichloromethane. The organic layer was washed with 5% NaHCO3 solution and water, dried over sodium sulfate and then evaporated under vacuum. The oily residue was chromatographed on silica gel using ethyl acetate as eluant to give pure title compound in 86% yield (330 mg).

$C_{23}H_{20}N_2O_4$ (MW 388.43); FD-MS m/z 388 (100[M]+), 100 (6[$CH_3CH_2OCOCHCH_2$]+); NMR δ ppm (DMSO-$d_3$): 1.16 (t, J=7.0 Hz, 3H), 1.67 (d, J=6.7 Hz, 3H), 4.17 (m, 2H), 5.31 (q, J=6.7 Hz, 1H), 6.67 (ddd, J=1.9/7.6/7.6 Hz, 1H), 6.85 (d, J=7.6 Hz, 1H), 6.94 (d, J=7.6 Hz, 1H), 7.1–7.2 (m, 2H), 7.59 (dd, J=4.1/8.5 Hz, 1H), 7.84 (d, J=8.2 Hz, 1H), 7.97 (s, 1H), 8.31 (dd, 1.7/8.5 Hz, 1H), 8.95 (dd, J=1.7/4.1 Hz, 1H), 10.62 (s, 1H).

By proceeding analogously the following compounds can be prepared:

5-[2-(dimethylamino)ethylamino]-3-(4-quinolylmethylen)-2-oxindole;

5-[2-(morpholino)ethylamino]-3-(4-quinolylmethylen)-2-oxindole; and

5-[2-(glycylamino)ethylamino]-3-(4-quinolylmethylen)-2-oxindole.

EXAMPLE 2
2-[5-(2-oxindol-3-ylidenemethyl)quinol-8-yloxy]propionic acid sodium salt To a suspension of 2-[5-(2-oxindol-3-ylidenemethyl) quinol-8-yloxy]propionic acid ethyl ester (150 mg, 0.39 mmol) in dioxane (15 ml) was added dropwise 2N sodium hydroxide (1.0 ml, 2 mmol) and the reaction mixture was stirred for another 1 h at room temperature. The crystalline precipitate was filtered and dried to give pure title compound in 73.8% yield (110 mg).

FD-MS m/z: 360 (100[M]+), 342 (17[M-H20]+); NMR $\delta$ ppm (DMSO-$d_3$) 1.65 (d, J=6.7 Hz, 3H), 5.15 (q, J=6.7 Hz, 1H), 6.69 (t, J=7.6 Hz, 1H), 6.85 (d, J=7.6 Hz, 1H), 6.97 (d, J=7.6 Hz, 1H), 7.1–7.2 (m, 2H), 7.60 (dd, J=4.1/8.8 Hz, 1H), 7.86 (d, J=7.9 Hz, 1H), 7.97 (s, 1H), 8.32 (dd, J=1.8/8.8 Hz, 1H), 8.95 (dd, J=1.8/4.1 Hz, 1H), 10.64 (s, 1H).

EXAMPLE 3

2-[5-(2-oxindol-3-ylidenemethyl)cquinol-8-yloxy] propionamide.

To a solution of 2-[5-(2-oxindol-3-ylidenemethyl)quinol-8-yloxy]propionic acid ethyl ester (120 mg, 0.31 mmol) in THF (5 ml) were added at room temperature under stirring ammonium hydroxide 28% (10 ml) and ammonium chloride (1.0 g). The mixture was stirred for another 48 h, then diluted with dichloromethane and acidified with 1N hydrochloric acid. The organic layer was washed twice with water, dried over sodium sulfate and concentrated under reduced pressure. The residue was crystallized from ethyl acetate to give pure title compound in 44.9% yield (50 mg).

EI-MS m/z: 359 (16[M]+), 315 (100[M-$NH_2$CO]+), 288 (59[M-$NH_2$COCH$CH_2$]+), 271 (30 [M-$NH_2$COCH$CH_2$-OH]+).

NMR $\delta$ ppm (DMSO-$d_3$): 1.61 (d, J=6.7 $H_z$, 3H), 1.62(d, J=6.7$H_z$, 3$H_E$), 4.95 (q, J=6.7 $H_z$, 1H, 1$H_E$), 6.70 (ddd, J=1.1/7.7/7.7$H_z$, 1$H_E$), 6.85 (d, J=7.6$H_z$, 1$H_E$), 6.98 (d, J=7.6Hz, 1$H_E$), 7.17 (ddd, J=1.1/7.6/7.6 $H_z$, 1$H_E$), 7.22 (d, J=8.2$H_z$, 1$H_z$), 7.28 (d, J=8.2$H_z$, 1$H_E$), 7.09 and 7.77 (two s, 2$H_E$, 2$H_z$), 7.55–7.70 (m, 1$H_E$, 1$H_z$), 7.87 (m, 1$H_E$, 1$H_z$), 7.97 (s, 1$H_E$) 8.34 (s, 1$H_z$), 8.34 (dd, J=1.8/8.7$H_z$, 1$H_E$), 8.51 (d, J=8.2 $H_z$, 1$H_z$), 8.70 (dd, J=1.6/8.7 $H_z$, 1$H_z$), 8.9–9.0 (m, 1$H_E$, 1$H_z$), 10.53 (S, 1$H_z$), 10.65 (s, 1$H_E$).

EXAMPLE 4

N-{2-[5-(2-oxindol-3-ylidenemethyl)quinol-8-yloxy] propionyl} alanine methylester.

To a solution of 2-[5-(2-oxindol-3-ylidenemethyl)quinol-8-yloxy]propionic acid (100 mg, 0.28 mmol), L-alanine methyl ester hydrochloride (40 mg, 0.29 mmol) and triethylamine (0.4 ml) in THF (10 ml) was added N,N'-dicyclohexylcarbodiimide (60 mg, 0.29 mmol) at room temperature under stirring. The stirring was continued for 15 h, then the mixture was filtered and the filtrate evaporated under vacuum. The residue was chromatographed on silica gel using as eluant ethylacetate methanol (9:1) to give pure title compound in 44.1% yield (55 mg).

$C_{25}H_{23}N_3O_5$ calcd: C67.41 H5.20 N9.43; found: C67.35 H5.22 N9.35; MS m/z 445.

By proceeding analogously the following compounds can be prepared:

N-[3-(8-hydroxyquinol-5-ylmethylen)-2-oxindol-5-ylcarbonyl] glycinamide;

N-[3-(8-hydroxyquinol-5-ylmethylen)-2-oxindol-5-ylcarbonyl] alaninamide; and 5-(2-piperidylacetyl)-3-(8-hydroxyquinol-5-ylmethylen)-2-oxindole.

EXAMPLE 5

N-{2-[5-(2-oxindol-3-ylidenemethyl)quinol-8-yloxy] propionyl} alanine sodium salt.

To a solution of N-{2-[5-(2-oxindol-3-ylidenemethyl) quinol-8-yloxy]propionyl} alanine methyl ester (50 mg, 0.11 mmol) in THF (10 ml) was added dropwise 2N sodium hydroxide (0.1 ml) at 0–50° C. After 4h stirring at room temperature THF (100 ml) was added, the organic layer washed 3 times with saturated sodium chloride solution, dried over magnesium sulfate and concentrated under vacuum. The residue was taken up in 5% sodium bicarbonate (10 ml) and chromatographed on a LoBar RP18 column using as eluant water/methanol (7:3) to give pure title compound in 84-yield (42 mg).

FAB-MS m/z 498 (70 [M+2Na−H]+), 476 (100 [M+Na]+); NMR $\delta$ ppm (DMSO-$d_3$): 1.19 (d, J=6.7$H_z$, 3$H_E$+3$H_z$), 1.5–1.6 (m, 3$H_E$3$H_z$), 3.63 (q, J=6.7$H_z$, 1$H_E$1$H_z$), 4.9–5.1 (m, 1$H_E$1$H_z$), 6.70 (ddd, J=7.6/7.6/0.9$H_z$, 1$H_E$), 6.80 (d, 7.6$H_z$, 1$H_z$), 6.84 (d, J=7.6$H_z$, 1$H_E$), 6.9–7.05 (m, 1$H_E$1$H_z$), 7.1–7.25 (m, 1$H_E$+2$H_z$), 7.28 (d, J=8.2$H_z$, 1$H_E$), 7.55–7.65 (m, 1$H_E$ +1$H_z$), 7.85 (M, 1$H_E$+1$H_z$) 7.97 (S, 1$H_E$), 8.05 (dr , J=5.9$H_z$, 1$H_E$+1$H_z$), 8.32 (dd, J=1.7$H_z$, 1$H_E$), 8.33 (s, 1$H_z$), 8.51 (d, J=8.5$H_z$, 1$H_z$), 8.69 (dd, J=8.5/1.5$H_z$, 1$H_z$), 8.9–9.0 (m, 1$H_E$1$H_z$), 10.55 (bS, 1$H_z$), 10.65 (bS, 1 $H_E$)

EXAMPLE 6

2- [5-(2-oxindol-3-ylidenemethyl) quinol-8-yloxy] acetic acid ethyl ester

To a solution of 8-hydroxyquinoline-5-carbaldehyde (170 mg, 0.98 mmol) in DMF (5 ml) were added anhydrous potassium carbonate (150 mg) and 2-bromoacetic acid ethyl ester (0.12 ml, 180 mg, 1.08 mmol) at room temperature and the stirring was continued for 1 h. Then the reaction mixture was diluted with dichloromethane, the organic layer was washed several times with water, dried over sodium sulfate and then evaporated under vacuum. The residue was chromatographed on silica gel with ethyl acetate/cyclohexane (9:1) as eluant; to give 190 mg (74.8% yield) of pure 2-(5-formylquinol-8-yloxy)acetic acid ethyl ester.

To a solution of the above obtained compound (190 mg, 0.73 mmol) in ethanol (15 ml) were added 2-oxindole (120 mg, 0.9 mmol) and piperidine (0.085 ml) and the mixture was stirred for 3 h at 80° C. After cooling dichloromethane was added, the organic layer washed 3 times with water, dried over sodium sulfate and concentrated under reduced pressure to give crystals, which were filtrated, washed with ice-cooled dichloromethane and dried. Yield 150 mg corresponding to 54.90%.

$C_{22}H_{18}N_2O_4$ calcd: C70.58 H4.85 N7.48; found: C70.33 H4.65 N7.40; MS M/z 374.

EXAMPLE 7

2-[5-(2-oxindol-3-ylidenemethyl)quinol-8-yloxy] acetic acid sodium salt

To a solution of 2-[5-(2-oxindol-3-ylidenemethyl)quinol-8-yloxy] acetic acid ethyl ester (150 mg, 0.40 mmol) in dioxane (20 ml) was added 2N sodium hydroxide (2 ml) and the mixture was stirred for 1 h at room temperature. The resulting crystals were separated by filtration, washed with dioxane and dried. Thus pure title compound was obtained in 81.5% yield (120 mg).

$C_{20}H_{13}N_2O_4Na$ calcd: C65.22 H3.56 N7.60 Na6.24; found: C65.15 H3.45 N7.35 Na6.13; MS m/z 368

EXAMPLE 8

N-{2-[5-(2-oxindol-3-ylidenemethyl)quinol-8-yloxy] acetyl} alanine methyl ester.

To a solution of 2-[5-(2-oxindol-3-ylidenemethyl)quinol-8-yloxy] acetic acid sodium salt (120 mg, 0.33 mmol), L-alanine methyl ester hydrochloride (100 mg, 0.72 mmol) and triethylamine (0.07 ml) in DMF (10 ml) was added at room temperature N,N'-dicyclohexylcarbodiimide (100 mg, 0.48 mmol) and the stirring was continued overnight. The reaction mixture was filtered and the filtrate concentrated under reduced pressure. The oily residue was taken up in dichloromethane, the organic phase washed 3 times with water, dried over sodium sulfate and concentrated under reduced pressure. The residue was chromatographed on silica gel using as eluant ethyl acetate/methanol (95:5) to give pure title compound in 70% yield (100 mg). $C_{24}H_{21}N_3O_5$ calcd: C66.81 H4.91 N9.74; found: C66.55 H4.56 N9.65; MS m/z 431.

EXAMPLE 9

N-{2-[5-(2-oxindol-3-ylidenemethyl)quinol-8-yloxy]acetyl} alanine sodium salt.

To a solution of N-{2-[5-(2-oxindol-3-ylidenemethyl)quinol-8-yloxy]acetyl} alanine methyl ester (50 mg, 0.12 mmol) in pyridine (5 ml) was added lithium iodide (65 mg) at 120° C. and the stirring was continued for another 6 h at this temperature. After cooling the solvent was removed under reduced pressure, the residue taken up with 5% sodium bicarbonate (25 ml) and chromatographed on a LoBar RP8 column with water/methanol 7:3 as eluant. After freeze-drying 45 mg of title compound was obtained (88w yield).

FAB-MS m/z: 462 (100[M+Na]+), 440 (40[MH]+) NMR δ ppm (DMSO-$d_3$): 1.20 (d, J=6.7$H_z$, 3$H_E$+3$H_z$); 3.73 (q, J=6.7$H_z$, 1$H_E$+1$H_z$), 4.76 (m, $^2H_E{}^2H_z$), 6.69 (ddd, J=7.6/7.6/0.9$H_z$, 1$H_z$), 6.81 (d, J=7.6$H_z$, 1$H_z$), 6.85 (d, J=7.6$H_z$, 1$H_E$), 6.9–7.05(m, 1$H_E$+1$H_z$), 7.1–7.3 (m, 1$H_E$+2$H_z$), 7.31 (d, J=8.2$H_z$, 1$H_E$), 7.6–7.7 (m, 1$H_E$+1$H_z$), 7.86 (m, 1$H_E$+1$H_z$), 7.98 (s, 1$H_E$), 8.03 (m, 1$H_E$+1$H_z$), 8.32 (dd, J=1.5/8.6$H_z$, 1$H_E$), 8.34 (s, 1$H_z$), 8.53 (d, J=8.2$H_z$, 1$H_z$), 8.70 (dd, J=1.8$H_z$, 1$H_z$), 8.9–9.0 (m, 1$H_E$+1$H_z$), 10.55 (bs, 1$H_z$), 10.65 (bs, 1$H_E$).

EXAMPLE 10

2-[3-(8-benzyloxyquinol-5-ylmethylen)-2-oxindol-1-yl] acetic acid ethyl ester.

To a solution of 8-hydroxyquinoline-5-carbaldehyde (346 mg, 2 mmol) in acetone (15 ml) anhydrous potassium carbonate (300 mg, 2.2 mmol) and benzylbromide (0.25 ml, 360 mg, 2.1 mmol) were added at 50° C. and the stirring was-continued for other 4 h at this temperature. The solvent was removed under reduced pressure, the residue taken up with dichloromethane, the organic layer washed several times with water, dried (sodium sulfate) and evaporated under vacuum. The residue was chromatographed on silica gel using as eluant ethylacetate/cyclohexane (2:3) to give 290 mg (55% yield) of 8-benzyloxyquinoline-5-carbaldehyde. The above obtained compound (290 mg, 1.1 mmol) was dissolved in ethanol (10 ml), then 2-oxindole (170 mg, 1.28 mmol) and piperidine (0.15 ml) were added and the, mixture maintained for 4 h at about 60° C. After cooling the precipitate was filtered, washed with cold ethanol and dried to give 300 mg (72% yield) of raw 3-(8-benzyloxyquinol-5-ylmethylen)-2-oxindole.

To a solution of 3-(8-benzyloxyquinol-5-ylmethylen)-2-oxindole (140 mg, 0.37 mmol) in acetone (10 ml) was added 2-bromoacetic acid ethyl ester (151 mg, 0.9 mmol) and anhydrous potassium carbonate (150 mg) and the reaction mixture was stirred for 8 h at 50° C. Then the mixture was concentrated under vacuum, the residue taken up with dichloromethane, the organic phase washed several times with water, dried and evaporated. The residue was crystallized from ethyl acetate to give 150 mg (87% yield) of title compound.

$C_{29}H_{24}N_2O_4$ calcd: C74.98 H5.21 N6.03; found: C74.65 H5.15 N5.95; MS m/z 464.

EXAMPLE 11

2-[3-(8-benzyloxyquinol-5-ylmethylen)-2-oxindol-1-yl] acetic acid sodium salt.

To a solution of 2-[3-(8-benzyloxyquinol-5-ylmethylen)-2-oxindol-1-yl] acetic acid ethyl ester (100 mg, 0.22 mmol) in THF (10 ml) was added 2N sodium hydroxide (0.5 ml) and the mixture was stirred for 4 h at room temperature. Then the mixture was filtered, the residue washed with THF and dried.

Thus 90 mg (91% yield) of title compound was obtained. $C_{27}H_{19}N_2O_4Na$ calcd: C70.74 H4.18 N6.11 Na5.02 found: C70.65 H4.05 N6.01 Na4.95 MS m/z 458.

EXAMPLE 12

N-{2-[3-(8-benzyloxyquinol-5-ylmethylen)-2-oxindol-1-yl]acetyl}alanine methyl ester To a solution of 2-[3-(8-benzyloxyquinol-5-ylmethylen)-2-oxindol-1-yl] acetic acid sodium salt (50 mg, 0.11 mmol), benzotriazol-1-yloxytrispyrrolidinophosphonium hexafluorophosphate (50 mg, 0.10 mmol) and triethylamine (11 mg, 0.11 mmol) in dichloromethane (10 ml) was added L-alanine methyl ester hydrochloride (20 mg, 0.14 mmol) and the mixture was stirred for 2 h at room temperature. Then dichloromethane was added, the organic layer washed 3 times with water, dried over sodium sulfate and concentrated under vacuum. The residue was chromatographed on silica gel using as eluant ethylacetate/cyclohexane (8:2) to give 45 mg (78.5% yield) of title compound.

$C_{31}H_{27}N_3O_5$ calcd: C71.39 H5.22 N8.06; found: C71.25 H4.95 N7.96; MS m/z 521

EXAMPLE 13

N-{2-[3-(8-hydroxyquinol-5-ylmethylen)-2-oxindol-1-yl] acetyl}alanine methyl ester To a solution of N-{2-[3-(8-benzyloxyquinol-5-ylmethylen)-2-oxindol-1-yl]acetyl}alanine methyl ester (45 mg, 0.09 mmol) in trifluoroacetic acid (5 ml) was added trifluoromethanesulfonic acid (0.1 ml) and the mixture was stirred at 0–5° C. for 0.5 h. Then dichloromethane was added, the mixture neutralized with 5% $NaHCO_3$ and the organic layer concentrated under vacuum to give 30 mg of title compound (77% yield).

FD-MS m/z 431 (100 [M]+), 346 (16 [M-CH ($CH_3$) $COOCH_3+_2H$]+); NMR δ ppm (DMSO-$d_3$) 1.29 (d, J=7.2$H_z$, 3H), 3.62 (s, 3H), 4.31 (q, J=7.2$H_z$, 1H), 4.43, 4.50 (two d, J=16.7$H_z$, 2H), 6.80 (ddd, J=7.5/7.5/0.7$H_z$, 1H), 6.88 (d, J=7.8$H_z$, 1H), 7.12 (d, J=7.5$H_z$, 1H), 7.25 (ddd, J=7.5/7.8/1.0 $H_z$, 1H), 7.33 (d, J=8.2$H_z$, 1H), 7.76 (dd, J=4.4/8.5$H_z$, 1H), 9.00 (dd, J=1.4/4.4$H_z$, 1H), 11.0 (bs, 1H).

EXAMPLE 14

5-alanylamino-3-(8-hydroxyquinol-5-ylmethylen)-2-oxindole.

To a stirred solution of 5-nitroindole (4 g, 24.6 mmol) in 200 ml of t-butanol was added portionwise pyridinium bromide perbromide (30 g, 93 mmol) over a period of 0.5 h. The reaction mixture was stirred at room temperature overnight, then the t-butanol was removed and the resulting residue dissolved in ethyl acetate/water (500/500 ml). The organic layer was separated and the aqueous layer was extracted with 300 ml of ethyl acetate. The organic extracts were washed with water, dried over sodium sulfate anhydrous and concentrated in vacuum to give 8. 5 g of less polar compound that was crystallized from ethyl acetate to give 7.5 g of dibromoderivative. Reduction of this compound with 10 equivalents of zinc dust in 80 ml of acetic acid at room temperature for 3h gave 5-amino-2-oxindole in good yields (3 g, 82%).

EI-MS m/z: 148 (100, [M]+), 120 (56, (M-CO]+), 119 (94, (M-CO-H]+), 105 (22, [M-NHCO]+).

To a solution of 5-amino-2-oxindole (2 g, 13.5 mmol) in 80 ml of water/dioxane 3:1 was added 1N sodium hydroxide until obtaining pH 10 and then di-t-butyl pyrocarbonate (3.5 g, 16.2 mmol). The reaction mixture was stirred for 3 h maintaining the pH at 10. After extraction with 3×100 ml of ethyl acetate the extracts were dried over sodium sulfate and then evaporated to obtain 2.4 g of 5-t-butoxycarbonylamino-2-oxindole (71% yield).

FD-MS m/z: 248 (100, [M]+), 191 (18, M-C4H9]+), 147 (5, [M-Me3COCO]+);

NMR δ ppm (DMSO-d$_3$): 1.49 (s, 9H), 3.87 (s, 3H), 6.72 (d, J=8.4H$_z$, 1H), 6.86 (dd, J=2.2/8.8H$_z$, 1H), 7.12 (dd, J=1.8/8.4H$_z$, 1H), 7.40 (d, J=8.8H$_z$, 1H), 7.54 (d, J=2.2H$_z$, 1H), 7.78 (d, J=1.8H$_z$, 1H), 7.92 (s, 1H), 8.87 (bs, 1H), 9.38 (s, 1H), 10.25 (s, 1H), 11.8 (bs, 1H).

To a solution of 5-t-butoxycarbonylamino-2-oxindole (630 mg, 2.5 mmol) and 8-hydroxyquinoline-5-carbaldehyde (450 mg, 2.6 mmol) in absolute alcohol was added piperidine (0.26 g, 2.6 mmol). The reaction was carried out at 80° C. for 3 h. The solvent was evaporated and the residue was purified by silica gel chromatography (eluant cyclohexane/ethylacetate 2:3) thus giving 800 mg of 5-(t-butoxycarbonylamino)-3-(8-hydroxyquinol-5-ylmethylen)-2-oxindole.

The above obtained compound (800 mg) was solubilized in 10 ml of dichloromethane, then 40 ml of trifluoroacetic acid was added and the mixture was stirred for 1 h at room temperature. The solvent was evaporated and the residue was crystallized from diethyl ether to give 683 mg of 5-amino-3-(8-hydroxyquinol-5-ylmethylen)-2-oxindole (90% yield).

To a solution of 5-amino-3-(8-hydroxyquinol-5-ylmethylen)-2-oxindole (497 mg, 1.64 mmol) and of t-butoxycarbonyl-L-alanine (360 mg, 1.9 mmol in 80 ml of THF were added 950 mg (1.82 mmol) of benzotriazol-1-yloxytripyrrolidinophosphoniun hexafluorophosphate and 0.2 ml (1.87 mmol) of N-methylmorpholine. The reaction was maintained at room temperature for 4 h. After evaporation of the solvent the residue was purified by flash chromatography with cyclohexane/ethyl acetate 3:7. The evaporated eluant was solubilized in dichloromethane, 10 ml of trifluoroacetic acid was added and the mixture stirred at room temperature for 1 h. After the usual workup pure title compound was obtained in 80% yield (491 mg).

$C_{21}H_{18}N_4O_3$ calcd: C67.37 H4.85 N14.97; found: C67.25 H4.55 N14.85; MS m/z 374.

By proceeding analogously the following compounds can be prepared:
5-glycylamino-3-(8-hydroxyquinol-5-ylmethylen)-2-oxindole;
5-threonylamino-3-(8-hydroxyquinol-5-ylmethylen)-2-oxindole;
5-glutamylamino-3-(8-hydroxyquinol-5-ylmethylen)-2-oxindole;
5-(t-butoxycarbonylamino-3-(8-hydroxyquinol-5-ylmethylen)-2-oxindole.

EXAMPLE 15

5-(3,3-dimethylguanidino)-3-(4-quinolylmethylen)-2-oxindole.

To a solution of 5-amino-3-(4-quinolylmethylen) -2-oxindole (431 mg, 1.5 mmol) in DMF (100 ml) containing triethylamine (202 mg, 2 mmol) was added 1-t-butoxycarbonyl-3,3-dimethylthiourea (409 mg, 2 mmol) and HgCl2 (543 mg, 2 mmol). The mixture was stirred at room temperature for 1 h and then filtered on a pad of celite. The residue was washed with ethyl acetate, the organic layer washed several times with water, dried and evaporated to dryness. The residue was chromatographed on silica gel using as eluant ethyl acetate/cyclohexane 2:1. The above obtained BOC-derivative was taken up in trifluoroacetic acid (10 ml) and then stirred for 1 h at room temperature. Ethyl acetate was added, the organic layer washed with 1N sodium hydroxide and brine, dried and evaporated. The residue was chromatographed on a LoBar RP18 column with water as eluant to give pure title compound after freeze-drying. Yield 50% (268 mg).

$C_{21}H_{19}N_5O$ calcd: C70.57 H5.36 N19.59; found: C70.55 H5.25 N19.49; MS m/z 357.

EXAMPLE 16

5-(dimethylaminomethylenamino)-3-(4-quinolylmethylen)-2-oxindole

To a solution of 5-amino-3-(4-quinolylmethylen)-2-oxindole (287 mg, 1 mmol) and triethylamine (121 mg, 1.2 mmol) in THF (20 ml) was added portionwise at, 0° C. chlorodimethyl-formimminium chloride (154 mg, 1.2 mmol) and the stirring was continued at room temperature for 1 h. Then the reaction mixture was diluted with dichloromethane, the organic layer washed with brine, dried over sodium sulfate and concentrated under vacuum. The residue was chromatographed on silica gel (eluant ethyl acetate/methanol 1:1) to give pure title compound in 60% yield (205 mg).

$C_{21}H_{18}N_4O$ calcd: C73.67 H5.30 N16.36; found: C73.65 HB.31 N16.25; MS m/z 342.

EXAMPLE 17

Tablets each weighing 0.150 g and containing 25 mg of the active substance, can be manufactured as follows:

Composition (for 10,000 tablets): 2-[5-(2-oxindol-3-ylidenemethyl)quinol-8-yloxy]

| propionic acid ethyl ester | 250 | g |
| Lactose | 800 | g |
| Corn starch | 415 | g |
| Talc powder | 30 | g |
| Magnesium stearate | 5 | g |

The 2-[5-(2-oxindol-3-ylidenemethyl)quinol-8-yloxy] propionic acid ethyl ester, the lactose and half of the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 18

Capsules, each dosed at 0.200 g and containing 20 mg of the active substance can be prepared.

Composition for 500 capsules: 2-[5-(2-oxindol-3-ylidenemethyl)quinol-8-yloxy]

| propionamide | 10 | g |
| Lactose | 80 | g |
| Corn starch | 5 | g |
| Magnesium stearate | 5 | g |

This formulation is encapsulated in two-piece hard gelatin capsules and dosed at 0.200 g for each capsule.

We claim:

1. A Quinolylmethylen-oxindole derivative having the following formula (I)

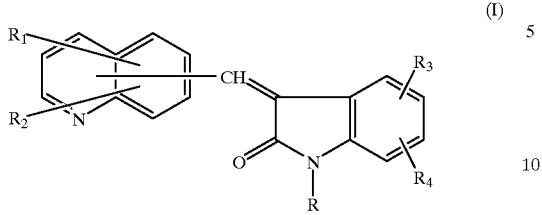

wherein
R is H or —(CH$_2$)$_n$—COR$_7$ group in which n is an integer of 1 to 4 and R$_7$ is hydroxy, amino, C$_1$–C$_6$ alkoxy or —NR$_5$R$_6$ in which one of R$_5$ and R$_6$ is hydrogen or C$_1$–C$_6$ alkyl and the other is C$_1$–C$_6$ alkyl or R$_5$ and R$_6$ taken together with the N atom to which they are linked form a 5 to 7 membered saturated heteromonocycle or R$_7$ is a N-terminally linked peptidyl residue containing from 1 to 3 aminoacids in which the terminal carboxyl group may be present as such, as amide, as alkali metal salt or as a C$_1$–C$_4$ alkyl ester; one or two of R$_1$, R$_2$, R$_3$ and R$_4$, which may be the same or different, are selected independently from:
a) —X—(CH$_2$)$_m$—NH$_2$, —X—(CH$_2$)$_m$—NR$_5$R$_6$ or —X—(CH$_2$)$_m$—NHR$_8$ group, in which X is —O—, —S— or —NH—, m is an integer of 2 to 4, R$_5$ and R$_6$ are as defined above, and R$_8$ is C$_2$–C$_6$ alkanoyl or a C-terminally linked peptidyl residue containing from 1 to 3 aminoacids wherein the terminal amino group is either free or protected or in an alkylated form to provide a —NR$_5$R$_6$ group in which R$_5$ and R$_6$ are as defined above;
b) —NH—C(=NH)—NR$_5$R$_6$, —NH—C(=NH)—NHR$_8$, —N=CH—NH$_2$, —N=CH—NR$_5$R$_6$ or —N=CH—NHR$_8$ group in which R$_5$, R$_6$ and R$_8$ are as defined above;
c) —X—(CH$_2$)$_n$—COR$_7$ group wherein X and R$_7$ are as defined above and n is an integer of 1 to 4;
d) —COR$_a$ or —COR$_9$ group in which R$_a$ is a N-terminally linked peptidyl residue containing from 1 to 3 aminoacids in which the terminal carboxyl group may be present as such, as amide, as alkali metal salt or as a C$_1$–C$_4$ alkyl ester and R$_9$ is a —(CH$_2$)$_p$—NH$_2$, —(CH$_2$)$_p$—NR$_5$R$_6$ or —(CH$_2$)$_p$—NHR$_8$ group in which p is 1 or 2 and R$_5$, R$_6$ and R$_8$ are as defined above;
e) —Y—CO—Y'—R$_{10}$ group wherein each of Y and Y', (which may be same or different) is —NH— or —O— and R$_{10}$ is phenyl or C$_1$–C$_6$ alkyl unsubstituted or substituted by phenyl; and
f) —NHR$_8$ or —NHR$_{11}$ group in which R$_8$ is as defined above and R$_{11}$ is an amino protective group; and the others of R$_1$, R$_2$, R$_3$ and R$_4$, which may be the same or different, are chosen from hydrogen, halogen, amino, hydroxy, C$_1$–C$_6$ alkyl, C$_1$–C$_6$ alkoxy, phenyl-(C$_1$–C$_6$) alkoxy, carboxy, C$_1$–C$_6$ alkoxycarbonyl, C$_2$–C$_6$ alkanoyloxy, cyano and —NR$_5$R$_6$ in which R$_5$ and R$_6$ are as defined above; or a pharmaceutically acceptable salt thereof.

2. A compound according to claim 1, wherein:
R is H or —(CH$_2$)$_n$—COR$_7$ group in which n is 1 and R$_7$ is hydroxy, amino, C$_1$–C$_4$ alkoxy or R$_7$ is a N-terminally linked peptidyl residue containing 1 to 2 aminoacids in which the terminal carboxyl group is present as alkali metal salt or as a C$_1$–C$_4$ alkyl ester; one of R$_1$, R$_2$, R$_3$ and R$_4$ is a substituent selected from:
a') —X—(CH$_2$)$_m$—NH$_2$, —X—(CH$_2$)$_m$—NR$_5$R$_6$ or —X—(CH$_2$)$_m$—NHR$_8$ in which X is —NH—, m is 2, one of R$_5$ and R$_6$ is C$_1$–C$_4$ alkyl and the other is hydrogen or C$_1$–C$_4$ alkyl or R$_5$ and R$_6$ taken together with the nitrogen atom to which they are linked form a morpholine ring, and R$_8$ is a C-terminally linked peptidyl residue containing 1 or 2 aminoacids in which the terminal amino group is present as such;
b') —NH—C(=NH)—NR$_5$R$_6$, —N=CH—NR$_5$R$_6$ in which one of R$_5$ and R$_6$ is C$_1$–C$_4$ alkyl and the other is hydrogen or C$_1$–C$_4$ alkyl;
c') —X—(CH$_2$)$_n$—COR$_7$ in which X is —O—, n is 1 or 2, R$_7$ is hydroxy, C$_1$–C$_6$ alkoxy, amino or a N-terminally linked peptidyl residue containing 1 or 2 aminoacids;
d') —COR$_a$ group in which R$_a$ is as defined in claim 1; and
f') —NHR$_8$ or —NHR$_{11}$ in which R$_8$ is C$_2$–C$_4$ alkanoyl or a C-terminally linked peptidyl residue containing 1 or 2 aminoacids and R$_{11}$ is an amino protecting group; and the others of R$_1$, R$_2$, R$_3$ and R$_4$, which may be the same or different, are chosen from hydrogen, halogen, amino, hydroxy, C$_1$–C$_4$ alkyl, C$_1$–C$_4$ alkoxy, phenyl-(C$_1$–C$_4$)alkoxy, C$_1$–C$_4$ alkoxy-carbonyl, C$_2$–C$_4$ alkanoyloxy, cyano and C$_1$–C$_4$ alkylamino and di-C$_1$–C$_4$ alkylamino.

3. A compound selected from:
5-[2-(dimethylamino)ethylamino]-3-(4-quinolylmethylen)-2-oxindole;
5-[2-(morpholino)ethylaminol]-3-(4-quinolylmethylen)-2-oxindole;
5-[2-(glycylamino)ethylamino]-3-(4-quinolylmethylen)-2-oxindole;
5-(3,3-dimethylguanidino)-3-(4-quinolylmethylen)-2-oxindole;
5-(dimethylaminomethylenamino)-3-(4-quinolylmethylen)-2-oxindole;
2-[5-(2-oxindol-3-ylidenemethyl)quinol-8-yloxy]propionic acid ethyl ester;
2-[5-(2-oxindol-3-ylidenemethyl)quinol-8-yloxy]propionic acid;
2-[5-(2-oxindol-3-ylidenemethyl)quinol-8-yloxy] propionamide;
N-{2-[5-(2-oxindol-3-ylidenemethyl)quinol-8-yloxy] propionyl} alanine methyl ester;
N-{2-[5-(2-oxindol-3-ylidenemethyl)quinol-8-yloxy] propionyl} alanine;
2-[5-(2-oxindol-3-ylidenemethyl)quinol-8-yloxy] acetic acid ethyl ester;
2-[5-(2-oxindol-3-ylidenemethyl)quinol-8-yloxy] acetic acid;
N-{2-[5-(2-oxindol-3-ylidenemethyl)quinol-8-yloxy] acetyl} alanine methyl ester;
N-{2-[5-(2-oxindol-3-ylidenemethyl)quinol-8-yloxy] acetyl} alanine;
N-[3-(8-hydroxyquinol-5-ylmethylen)-2-oxindol-5-ylcarbonyl] glycinamide;
5-(2-piperidylacetyl)-3-(8-hydroxyquinol-5-ylmethylen)-2-oxindole;
N-[3-(8-hydroxyquinol-5-ylmethylen)-2-oxindol-5-ylcarbonyl] alaninamide;
5-(t-butoxycarbonylamino)-3-(8-hydroxyquinol-5-ylmethylen)-2-oxindole;
5-(glycylamino)-3-(8-hydroxyquinol-5-ylmethylen)-2-oxindole;
5-(alanylamino)-3-(8-hydroxyquinol-5-ylmethylen)-2-oxindole;

5-(threonylamino)-3-(8-hydroxyquinol-5-ylmethylen)-2-oxindole;

5-(glutamylamino)-3-(8-hydroxyquinol-5-ylmethylen)-2-oxindole;

2-[3-(8-benzyloxyquinol-5-ylmethylen)-2-oxindol-1-yl] acetic acid ethyl ester;

2-[3-(8-benzyloxyquinol-5-ylmethylen)-2-oxindol-1-yl] acetic acid;

N-{2-[3-(8-benzyloxyquinol-5-ylmethylen)-2-oxindol-1-yl] acetyl} alanine methyl ester; and N-{2-[3-(8-hydroxyquinol-5-ylmethylen)-2-oxindol-1-yl] acetyl} alanine methyl ester;

and the pharmaceutically acceptable salts thereof.

4. A process for producing a compound as defined in claim 1, the process comprising:

A) reacting an aldehyde of formula (II)

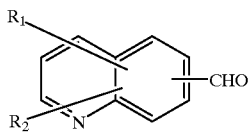

(II)

wherein $R_1$ and $R_2$ are as defined in claim 1, with a compound of formula (III)

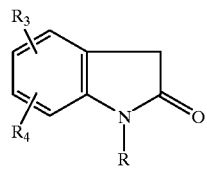

(III)

wherein $R_1$, $R_3$ and $R_4$ are as defined in claim 1; or

B) reacting a compound of formula (IV)

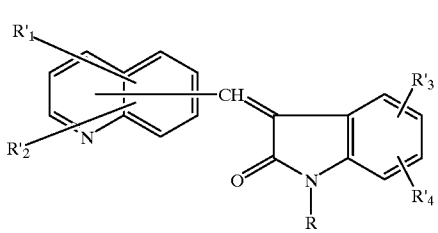

(IV)

wherein one or two of $R'_1$, $R'_2$, $R'_3$ and $R'_4$ are OH, —NH$_2$ or —SH and the others are as R, $R_1$, $R_2$, $R_3$ and $R_4$ as defined in claim 1, with an alkylating agent of formula (V) selected from Z—(CH$_2$)$_m$—NH$_2$;
Z—(CH$_2$)$_m$—NR$_5$R$_6$;
Z—(CH$_2$)$_m$—NHR$_8$ and
Z—(CH$_2$)$_n$—COR$_7$;

in which Z is a halogen atom and m, n, $R_5$, $R_6$, $R_7$ and $R_8$ are as defined in claim 1, thus obtaining a compound of formula (I) wherein one or two of $R_1$, $R_2$, $R_3$ and $R_4$ are as defined in claim 1 under a) or c); or C) reacting a compound of formula (VI)

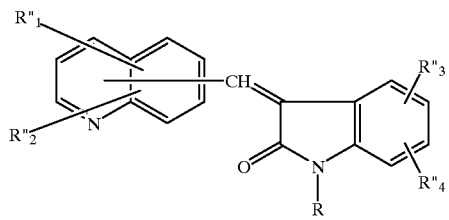

(VI)

wherein one or two of R", R"$_2$, R"$_3$ and R"$_4$ are —OH or —NH$_2$ and the others are as $R_1$, $R_2$, $R_3$ and $R_4$ as defined in claim 1, with an acylating agent of formula (VII) selected from

HOOC—Y'—R$_{10}$   (VII)

or a reactive carboxyl derivative thereof, wherein Y' and $R_{10}$ are as defined in claim 1, thus obtaining a compound of formula (I) wherein one or two of $R_1$, $R_2$, $R_3$ and $R_4$ are as defined in claim 1 under e);

D) reacting a compound of formula (VIII)

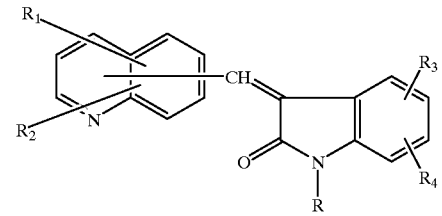

(VIII)

wherein R is H and $R_1$, $R_2$, $R_3$ and $R_4$ are as defined in claim 1, with an alkylating agent of formula (IX)

Z—(CH$_2$)$_n$—COR$_7$   (IX)

wherein Z, n and $R_7$ are as defined in claim 1, thus obtaining a compound of formula (I) wherein R is a —(CH$_2$)$_n$—COR$_7$ group;

E) reacting a compound of formula (X)

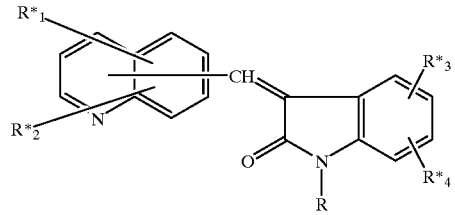

(X)

wherein one or two of $R^*_1$, $R^*_2$, $R^*_3$ and $R^*_4$ are amino or carboxy and the others are as $R_1$, $R_2$, $R_3$ and $R_4$ as defined in claim 1, with a peptide compound of formula $R_8$H and $R_a$H, wherein $R_8$ and $R_a$ are peptidyl residues as defined in claim 1, thus giving compounds of formula (I), wherein one or two of $R_1$, $R_2$, $R_3$ and $R_4$ are as defined in claim 1 under f) and d) respectively; and, if desired, converting a compound of formula (I) into another compound of formula (I), and/or, if desired, converting a compound of formula (I) into a pharmaceutically acceptable salt thereof, and/or, if desired, converting a salt of a compound of formula (I) into a free compound of formula (I), and/or, if desired, separating a mixture of isomers of a compound of formula (I) into the single isomers.

5. A pharmaceutical composition containing a suitable carrier and/or diluent, and, as an active principle, a compound as defined in claim 1.

6. A pharmaceutical composition, comprising:

a compound of formula (I) as defined in claim 1 or a pharmaceutically acceptable salt thereof, and an antitumor agent.

7. A method of treating a patient in need of a tyrosine kinase inhibitor, the method comprising administering to said patient a therapeutically effective amount of a compound of formula (I), as defined in claim 1 or a pharmaceutically acceptable salt thereof.

* * * * *

UNITED STATES PATENT AND TRADEMARK OFFICE
CERTIFICATE OF CORRECTION

PATENT NO. : 5,905,149
DATED : May 18, 1999
INVENTOR(S) : Carlo BATTISTINI, et al.

It is certified that error appears in the above-identified patent and that said Letters Patent is hereby corrected as shown below:

On the title page, item [54] and on top of column 1, lines 3-4, should read

--[54] SUBSTITUTED QUINOLYLMETHYLEN-OXINDOLE ANALOGUES AS TYROSINE KINASE INHIBITORS--

Signed and Sealed this

Eleventh Day of April, 2000

Q. TODD DICKINSON

Attest:

Attesting Officer

Director of Patents and Trademarks